US007858539B2

(12) United States Patent
Li et al.

(10) Patent No.: US 7,858,539 B2
(45) Date of Patent: Dec. 28, 2010

(54) PROCESSES FOR GENERATING HALAMINE COMPOUNDS ON TEXTILE SUBSTRATES TO PRODUCE ANTIMICROBIAL FINISH

(75) Inventors: Ling Li, Blue Bell, PA (US); Shulong Li, Spartanburg, SC (US); Jeffrey S. Lane, Moore, SC (US)

(73) Assignee: Milliken & Company, Spartanburg, SC (US)

( * ) Notice: Subject to any disclaimer, the term of this patent is extended or adjusted under 35 U.S.C. 154(b) by 749 days.

(21) Appl. No.: 11/784,711

(22) Filed: Apr. 9, 2007

(65) Prior Publication Data

US 2008/0248705 A1 Oct. 9, 2008

(51) Int. Cl.
B32B 27/04 (2006.01)
(52) U.S. Cl. ..................... 442/123; 8/115.59
(58) Field of Classification Search .................. 442/123
See application file for complete search history.

(56) References Cited

U.S. PATENT DOCUMENTS

| | | | |
|---|---|---|---|
| 3,488,701 A | 1/1970 | Herbes et al. | |
| 4,931,562 A | 6/1990 | Akabane | |
| 5,490,983 A | 2/1996 | Worley et al. | |
| 5,670,646 A | 9/1997 | Worley et al. | |
| 5,705,545 A | 1/1998 | Avar et al. | |
| 5,817,806 A | 10/1998 | Rossi et al. | |
| 5,882,357 A | 3/1999 | Sun et al. | |
| 5,889,130 A | 3/1999 | Worley et al. | |
| 5,902,818 A | 5/1999 | Worley et al. | |
| 6,020,491 A | 2/2000 | Worley et al. | |
| 6,077,319 A | 6/2000 | Sun et al. | |
| 6,162,452 A | 12/2000 | Worley et al. | |
| 6,241,783 B1 | 6/2001 | Sun | |
| 6,294,185 B1 | 9/2001 | Worley et al. | |
| 6,482,756 B2 | 11/2002 | Li | |
| 6,576,154 B1 | 6/2003 | Li | |
| 6,585,989 B2 | 7/2003 | Herbst et al. | |
| 6,770,287 B1 | 8/2004 | Sun et al. | |
| 2003/0056297 A1 | 3/2003 | Sun | |
| 2003/0064645 A1 | 4/2003 | Worley et al. | |
| 2004/0063831 A1 | 4/2004 | Sheppard et al. | |
| 2004/0086480 A1 | 5/2004 | Worley et al. | |
| 2004/0121681 A1 | 6/2004 | Quincy et al. | |
| 2004/0127667 A1 | 7/2004 | Worley et al. | |
| 2004/0191315 A1 | 9/2004 | Slattery et al. | |
| 2006/0148940 A1 | 7/2006 | Sun et al. | |
| 2007/0092724 A1* | 4/2007 | Li et al. ...................... 428/375 |

FOREIGN PATENT DOCUMENTS

| | | |
|---|---|---|
| EP | 0 352 221 A1 | 1/1990 |
| WO | WO 01/07550 A1 | 2/2001 |
| WO | WO 2005/058814 A2 | 6/2005 |

OTHER PUBLICATIONS

Chen et al., Antimicrobial Functions of N-Chloro-Hindered Amines, *Polymer Preprints*, 46(2): 835-836 (2005).
Chen et al., N-Chloro-Hindered Amines as Multifunctional Polymer Additives, *Macromolecules*, 38: 8116-8119 (2005).
Eknoian, M.W. et al., Novel Antimicrobial N-halamine Polymer Coatings Generated by Emulsion Polymerization. *Polymer* 1999, 40, 1367-71.
Qian. L. et al. Durable and Regenerable Antimicrobial Textiles: Improving Efficacy and Durability of Biocidal Functions, *J. Appl. Polym. Sci* 2004, 91, 2588-93.
Sun et al., The Chemistry of Functional Finishing: Self-decontaminating Textile Materials, *National Textile Center Research Briefs—Chemistry Competency* (Jun. 2003).
Sun et al., Chemistry of Functional Finishing: Self-decontaminating Textile Materials, *National Textile Center Research Briefs—Chemistry Competency* (Jun. 2004).
Sun et al., Chemistry of Functional Finishing: Self-decontaminating Textile Materials, *National Textile Center Research Briefs—Chemistry Competency* (Jun. 2005).
Sun et al., Synthesis, Characterization, and Antibacterial Activities of Novel N-Halamine Polymer Beads Prepared by Suspension Copolymerization, *Macromolecules*, 35: 8909-8912 (2002).
Sun et al., National Center Annual Report, NTC Project C02-CD06 (Nov. 2003).
Sun et al., National Center Annual Report, NTC Project C02-CD06 (Nov. 2004).
SciFinder Search Results for 1-chloro-2,2,6,6-tetramethyl-4-piperidinyl structures (2006).

* cited by examiner

*Primary Examiner*—Lynda Salvatore
(74) *Attorney, Agent, or Firm*—Robert M. Lanning

(57) ABSTRACT

Provided herein are processes for topically applying an antimicrobial finish to a textile substrate, such as a yarn, a fabric, a composite, or an assembled article (for example, a garment). Specifically, the antimicrobial finish is based on hindered amine compounds that are applied in an aqueous bath (such as a commercial or home laundry setting), using the factors of pH and compound solubility to promote the formation of a durable antimicrobial halamine finish. Advantageously, the antimicrobial finish, which may be applied to fabrics made of any of a variety of fiber types and combinations of fiber types, has been found to be durable to repeated launderings.

17 Claims, No Drawings

PROCESSES FOR GENERATING HALAMINE COMPOUNDS ON TEXTILE SUBSTRATES TO PRODUCE ANTIMICROBIAL FINISH

TECHNICAL FIELD

This disclosure is directed to processes for topically applying an antimicrobial finish to a textile substrate, such as a yarn, a fabric, a composite, or an assembled article (for example, a garment). Specifically, the antimicrobial finish is based on hindered amine compounds that are applied in an aqueous bath (such as a commercial or home laundry setting), using the factors of pH and compound solubility to promote the formation of a durable antimicrobial halamine finish. Advantageously, the antimicrobial finish, which may be applied to fabrics made of any of a variety of fiber types and combinations of fiber types, has been found to be durable to repeated launderings. Moreover, the antimicrobial properties may be renewed during subsequent launderings with an oxidative solution, for example, standard chlorine bleach.

BRIEF SUMMARY

Provided herein are several processes for imparting wash-durable antimicrobial properties to a textile substrate without adversely affecting the color, hand, or other physical properties of the substrate. The antimicrobial properties are the result of the presence of a hindered halamine on the surface of the textile substrate.

In a first embodiment, the process comprises the steps of:
(a) dissolving a hindered amine compound in an aqueous solution by adding acid to the hindered amine compound, thereby producing a solution containing up to about 30% by weight of solution of a protonated hindered amine compound;
(b) contacting a target textile substrate with the protonated hindered amine solution, for example, in the rinse cycle of a typical laundry process, thereby causing the protonated hindered amine to deposit on the surface of the textile substrate;
(c) deprotonating the hindered amine deposited on the target textile substrate by evaporating the acid used to protonate the hindered amine or by neutralizing the protonated hindered amine with an alkaline; and
(d) reacting the deposited, deprotonated hindered amine with an oxidative halogen-containing solution (e.g., bleach), for example, in the rinse cycle, to form a hindered halamine on the textile substrate.

In an alternate embodiment, where hydrogen peroxide is used in place of chlorine bleach, steps (a) through (c) are the same as those provided above. In step (d), a halide salt (such as sodium chloride) is added with hydrogen peroxide in place of halogenated bleach. Thus, step (d) is as follows: adding a halide salt and hydrogen peroxide to react with the deprotonated hindered amine to form a hindered halamine on the textile surface. In this embodiment, the halide from the salt reacts with peroxide to form an oxidative halogenated species. The oxidative halogenated species subsequently reacts with the deprotonated hindered amine to form a hindered halamine.

In yet another embodiment, such as may occur in a manufacturing environment, the process comprises the steps of:
(a) providing a textile substrate to be treated;
(b) preparing an aqueous bath containing from about 0.02% by weight to about 5.0% by weight of solution of a protonated hindered amine compound, where the aqueous bath further contains an acid that lowers the pH of the bath and assists in solubilizing the protonated hindered amine compound;
(c) saturating the textile substrate of (a) in the bath of (b);
(d) drying the textile substrate to volatilize the acid and deprotonate the hindered amine compound, thereby rendering the hindered amine compound insoluble in water or alkaline laundering conditions; and
(e) applying an oxidative halogen-containing solution, or a combination of hydrogen peroxide and a halide salt, to the textile substrate to react with the deprotonated hindered amine and form a hindered halamine.

DETAILED DESCRIPTION

Textile Substrates

The disclosure is directed to processes for producing antimicrobial treated textile materials. Such textile substrates may comprise a plurality of yarns, the yarns comprising a hindered halamine compound disposed on the exterior surface of the yarns and/or dispersed in the interior portion of the yarns.

The treated textile substrate may be any suitable textile material. The textile material may comprise a plurality of yarns provided in a knit or woven construction, or the textile material may comprise a plurality of fibers that are provided in a non-woven construction. Further, the treated textile substrate may be a composite having multiple layers, at least one of which has been treated with the halamine compounds described herein. Alternately, the textile substrate may be an assembled article, such as a garment, item of apparel (such as a hat or glove), sheet, item of napery (such as a napkin or tablecloth), or the like, which is treated after having been assembled.

The yarns or fibers from which the textile substrate is constructed may contain natural fibers, synthetic fibers, or any suitable combination thereof. Suitable fibers include, but are not limited to, cellulose (e.g., cotton and rayon), polyamides, polyesters, polyethylenes, polypropylenes, polyacrylics, cellulose acetate, polylactic acid, silk, wool, glass, polyaramids, and combinations thereof. In a preferred embodiment, the textile substrate comprises yarns comprising fibers selected from the group consisting of cellulose fibers (e.g., cotton and rayon), polyester fibers, polyamide fibers, and combinations thereof (e.g., blends of cotton and polyester fibers or blends of cotton and nylon fibers).

The textile substrate may be undyed or may be dyed before application of the present antimicrobial finish. Additionally, the textile substrate may be treated with various textile processing aids, such as softeners, wicking agents, anti-soil deposition agents, soil release agents, and the like, before, after, or simultaneously with the present antimicrobial finish.

Hindered Amine to Halamine Reaction

The hindered amine compound may be any suitable secondary hindered amine compound (i.e., a hindered amine compound having a hydrogen atom bonded to the nitrogen atom of the amine group). As utilized herein, the term "hindered amine" refers to a compound or moiety in which the carbon atoms adjacent to the nitrogen atom of the amine group do not have a hydrogen atom attached directly thereto. Preferably, the carbon atoms adjacent to the nitrogen atom of the hindered amine compound or moiety are not carbonyl carbons (i.e., a carbon atom having an oxygen atom double bonded thereto). The hindered amine compound may have any suitable molecular weight. The hindered amine compound may be monomeric or polymeric in chemical nature. Typically, monomeric hindered amines have a molecular weight of about 1,000 atomic mass units or less or about 500 atomic mass units or less. Typically, polymeric hindered amines have a molecular weight of greater than about 1,000 atomic mass units and, more preferably, are at least about 1,500 atomic mass units or at least about 2,000 atomic mass units. Where a plurality of hindered amine moieties are present in a polymeric hindered amine compound, the molecular weight is preferably greater than about 2,000 atomic mass units.

When reacted in the presence of acid, the hindered amine compound produces a "protonated hindered amine." In this compound, the nitrogen atom of the amine group takes on a positive charge, as the hydrogen ion ($H^+$, or proton) is bonded to the nitrogen atom of the hindered amine. We have discovered that unlike the hindered amine structures described herein, the protonated hindered amine compounds are water soluble, especially at low pH levels (that is, pH levels of from 0 to 6), making them useful as intermediate compounds in the present process.

As utilized herein, the term "halamine" refers to an amine derivative (e.g., a derivative of a secondary amine) in which a hydrogen atom attached to the nitrogen atom of the amine has been replaced with a halogen atom (e.g., a chlorine, bromine, or iodine atom). The halamine compounds described herein are not water soluble during normal laundry conditions, resulting in a high level of wash durability for the textile finishes containing such compounds. The halamine compounds contemplated herein have molecular weights that fall into the same parameters as those provided above for the hindered amine compounds.

The present process is believed to function based on a reaction scheme, which is generically shown below:

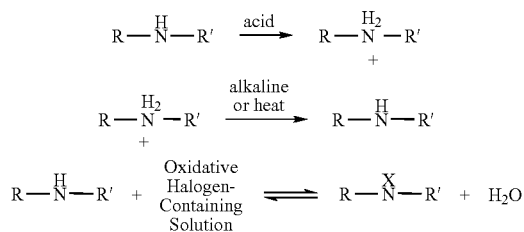

In this reaction, a hindered amine compound (examples of which will be provided below) reacts with an acid, preferably in an aqueous solution, to form a protonated hindered amine compound, thus resulting in a positive charge associated with the nitrogen atom. The protonated hindered amine compound, when added to a fabric rinse cycle, tends to deposit on the surface of the substrate (due to the residual presence of anionic surfactants from laundry detergents). When an oxidative halogen-containing solution is added to the rinse liquid, the pH increases, resulting in deprotonation of the hindered amine and promoting the deposition of the hindered amine onto the substrate and causing a reaction between the deprotonated hindered amine and the oxidative halogen. As a result, a halamine precipitate is formed on the surface of the textile substrate. In such structure, the X represents a chlorine atom, a bromine atom, or an iodine atom.

The term "oxidative halogen-containing solution" refers to a solution containing a halogen-containing species in which the halogen is in an oxidative valent state (i.e., a zero or positive valence state). Suitable oxidative halogen solutions include, but are not limited to, solutions of sodium hypochlorite, potassium hypobromite, sodium perchlorate, chlorine oxide, sodium periodate, iodine, bromine, and combinations thereof. Where the oxidative halogen-containing solution is not inherently basic (i.e., pH less than 6), a separate base may be added prior to, or simultaneously with, the addition of the oxidative halogen-containing solution. It has been found that even dilute aqueous solutions of a hypohalite (e.g., an aqueous solution containing from about 0.001% to about 1% by weight of a hypochlorite, such as sodium hypochlorite) are effective at converting the deprotonated hindered amine compound to a halamine compound, thus imparting antimicrobial properties to the treated textile substrate.

While not wishing to be bound to any particular theory, it is believed that at least a portion of the hindered amine compounds present on the treated textile material undergo a reaction with the halogen-containing species in the oxidative halogen solution in which the halogen species reacts with the nitrogen atom of the hindered amine compound to replace the hydrogen with a halogen atom, thereby producing a halamine. For example, upon exposure to a hypohalite solution, such a hindered amine compound (i.e., a compound conforming to one of structures (I)-(XI) in which X is hydrogen, as will be described as follows) is believed to undergo an equilibrium reaction in which a protonated hypohalite ion reacts with the nitrogen atom of the hindered amine to replace the hydrogen atom with a halogen atom and eliminate water.

Such a reaction using an aqueous hypochlorite solution can be represented by the following general reaction scheme:

Hindered Amine Compounds

Compounds having various different hindered amine structures may be used in the present process to form a halamine compound useful for imparting antimicrobial properties to a target textile substrate. In the case of hindered amine compounds, the "X" constituent in such structures represents a hydrogen atom. In the case of halamine compounds, the "X" constituent represents a chlorine atom, a bromine atom, or an iodine atom.

Structure (I)

In certain embodiments, the hindered amine or halamine compound conforms to structure (I):

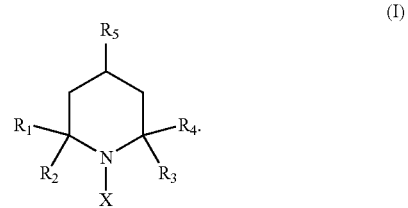

In structure (I), $R_1$, $R_2$, $R_3$, and $R_4$ are independently selected from the group consisting of $C_1$-$C_4$ alkyl groups, and $R_5$ is selected from the group consisting of a hydrogen atom, an alkyl group, an alkyl amine group, a cyclic amine group, an amide group, a cyclic amide group, an isocyanate group, a hydroxyl group, an ether group, an ester group, and combinations thereof. X represents a hydrogen atom, when the compound is a hindered amine. When the structure is a halamine, X represents a chlorine atom, a bromine atom, or an iodine atom Suitable hindered amine or halamine compounds conforming to structure (I) include, but are not limited to:
2,2,6,6-tetramethylpiperidine (CAS Registry Number 768-66-1);
4-chloro-2,2,6,6-tetramethylpiperidine;
4-bromo-2,2,6,6-tetramethylpiperidine (CAS Registry Number 67845-89-0);
2,2,6,6-tetramethyl-piperidin-4-ol, 4-isocyanato-2,2,6,6-tetramethylpiperidine (CAS Registry Number 84712-82-3);
N-butyl-2,2,6,6-tetramethylpiperidin-4-amine (CAS Registry Number 36177-92-1);
4,4-bis[(tert-butyl)dioxy]-2,2,6,6-tetramethylpiperidine (CAS Registry Number 75279-29-7);
N,N-bis-(2,2,6,6-tetramethyl-piperidin-4-yl)-propane-1,3-diamine (CAS Registry Number 63525-94-0);
N,N-bis-(2,2,6,6-tetramethyl-piperidin-4-yl)-hexane-1,6-diamine (CAS Registry Number 61260-55-7);
N'-(2,2,6,6-tetramethyl-piperidin-4-yl)-hexane-1,6-diamine (CAS Registry Number 72245-37-5);
2,2,6,6-tetramethylpiperidin-4-yl benzoate (CAS Registry Number 26275-88-7);
bis(2,2,6,6-tetramethyl-4-piperidyl)succinate (CAS Registry Number 62782-03-0);
3-dodecyl-1-(2,2,6,6-tetramethyl-piperidin-4-yl)-pyrrolidine-2,5-dione (CAS Registry Number 79720-19-7);
1,5-dioxa-spiro[5,5]undecane-3,3-dicarboxylic acid bis-(2,2,6,6-tetramethyl-piperidin-4-yl)ester (CAS Registry Number 110843-97-5);
2,6-bis-(2,2,6,6-tetramethyl-piperidin-4-yl)-hexahydro-2,3a,4a,6,7a,8a-hexaaza-cyclopenta [def]fluorine-4,8-dione (CAS Registry Number 109423-00-9);
N,N'-bis(2,2,6,6-tetramethylpiperidin-4-yl)-N,N'-diformyl-1,6-diaminohexane (CAS Registry Number 124172-53-8);
2,2,6,6-tetramethyl-4-piperidinecarboxylic acid 1,4-cyclohexanediylbis(methylene) ester (CAS Registry Number 70851-59-1);
2,2,6,6-tetramethyl-piperidin-4-yl methacrylate (CAS Registry Number 31582-45-3);
methyl-[3-(2,2,6,6-tetramethyl-piperidin-4-yloxy)-propyl]-silanediol (CAS Registry Number 164578-16-9);
N-(2,2,6,6-tetramethyl-piperidin-4-yl)stearamide (CAS Registry Number 37819-84-4);
bis(2,2,6,6-tetramethyl-piperidin-4-yl)sebacate (CAS Registry Number 52829-07-9);
bis(1,2,2,6,6-pentamethyl-piperidin-4-yl)sebacate (CAS Registry Number 41556-26-7);
methyl 1,2,2,6,6-pentamethyl-piperidin-4-yl sebacate (CAS Registry Number 82919-37-7);
4-hydroxy-2,2,6,6-tetramethyl-piperidine-4-carboxylic acid (CAS Registry Number 65402-65-5);
heptadecanoic acid 2,2,6,6-tetramethyl-piperidin-4-yl ester;
N,N'-1,6-hexanediylbis[N-(2,2,6,6-tetramethyl-piperidin-4-yl)-formamide (CAS Registry Number 124172-53-8);
N,N'-bis(1,1,3,3-tetramethylbutyl)-2,9,15,22-tetrakis(2,2,6,6-tetramethyl-piperidin-4-yl)-2,9,11,13,15,22,24,26,27,28-decaazatricyclo[21.3.1.1$^{10,14}$]octacosa-1(27),10,12,14 (28), 23,25-hexaene-12,25-diamine (CAS Registry Number 86168-95-8);
poly[(6-morpholino-s-triazine-2,4-diyl)[(2,2,6,6-tetramethyl-piperidin-4-yl)imino]-hexamethylene[(2,2,6,6-tetramethyl-piperidin-4-yl)imino)]] (CAS Registry Number 082451-48-7);
and combinations thereof.

When the hindered amine compound conforms to structure (I), the hindered amine compound preferably is poly[(6-morpholino-s-triazine-2,4-diyl)[(2,2,6,6-tetramethyl-piperidin-4-yl)imino]-hexamethylene[(2,2,6,6-tetramethyl-piperidin-4-yl) imino)]] (CAS Registry Number 082451-48-7).

Structure (II)

Suitable hindered amine or halamine compounds conforming to structure (I) also include those hindered amine or halamine compounds conforming to structure (II):

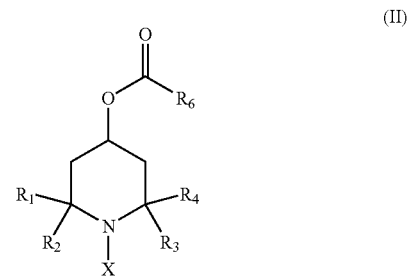

(II)

In structure (II), $R_1$, $R_2$, $R_3$, and $R_4$ are independently selected from the group consisting of $C_1$-$C_4$ alkyl groups, and $R_6$ is a $C_{11}$-$C_{20}$ alkyl group. A particular embodiment of a hindered amine compound conforming to structure (II) is a hindered amine light stabilizer sold under the name CYASORB® UV-3853 (available from Cytec Industries Inc.) (CAS Registry Number 167078-06-0), in which $C_1$-$C_4$ are methyl groups and the Rr groups are $C_{11}$-$C_{20}$ alkyl groups, predominantly $C_{16}$-$C_{18}$ alkyl groups.

Structure (III)

In certain embodiments, the hindered amine or halamine compound conforms to structure (III)

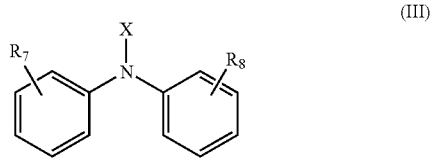

(III)

In structure (III), $R_7$ and $R_8$ are independently selected from the group consisting of a hydrogen atom, an alkyl group, an aryl group, an amine group, an amide group, and combinations thereof. Suitable hindered amine or halamine compounds conforming to structure (III) include, but are not limited to:
N-phenylnaphthalen-1-amine;
N-phenylnaphthalen-2-amine;
bis-[4-(1-phenyl-ethyl)-phenyl]-amine;
N-(1,3-dimethylbutyl)-N'-phenylbenzene-1,4-diamine,4-methylphenyl(4-anilino-phenyl)amido-sulfite;
and combinations thereof.

Structure (IV)

In certain embodiments, the hindered amine or halamine compound conforms to structure (IV):

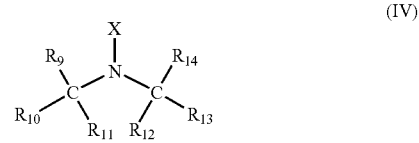

(IV)

In structure (IV), $R_9$, $R_{11}$, $R_{12}$, and $R_{14}$ are independently selected from the group consisting of $C_1$-$C_4$ alkyl groups, and $R_{10}$ and $R_{13}$ are independently selected from the group consisting of an alkyl group, an aryl group, an amine group, an amide group, and combinations thereof.

Structure (V)

In certain embodiments, the hindered amine or halamine compound conforms to structure (V):

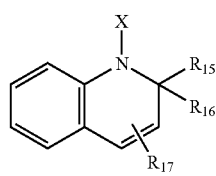

(V)

In structure (V), $R_{15}$ and $R_{16}$ are independently selected from the group consisting of $C_1$-$C_4$ alkyl groups, and $R_{17}$ is selected from the group consisting of a hydrogen atom, an alkyl group, an aryl group, an amine group, an amide group, and combinations thereof.

Suitable hindered amine or halamine compounds conforming to structures (IV) and (V) include, but are not limited to:
2,2-dimethyl-1,2-dihydroquinoline;
2,2,4-trimethyl-1,2-dihydroquinoline;
2,2,3,3-tetramethyl-1,2,3,4-tetrahydroquinoline;
2,2,3,3,4-pentamethyl-1,2,3,4-tetrahydroquinoline;
and combinations thereof.

Structure (VI)

In certain embodiments, the hindered amine or halamine compound conforms to structure (VI):

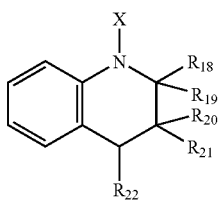

(VI)

In structure (VI), $R_{18}$, $R_{19}$, $R_{20}$, and $R_{21}$ are independently selected from the group consisting of $C_1$-$C_4$ alkyl groups, and $R_{22}$ is selected from the group consisting of a hydrogen atom, an alkyl group, an aryl group, an amine group, an amide group, and combinations thereof.

As an alternative to structures (I)-(VI) above, halamine compounds comprised of a plurality of secondary hindered amines may also be used. Using this approach, at least two, and preferably at least three, hindered amines are incorporated into the halamine structure. As utilized herein, the term "polymer" is used to describe any backbone structure, such as linear, branched, or cyclic chain structures, comprising a plurality of (e.g., at least two, preferably at least three) secondary hindered amine moieties covalently bonded to the backbone structure.

While not wishing to be bound to any particular theory, it is believed that a polymer comprising a greater number of secondary hindered amine moieties will exhibit a higher affinity toward the oxidative halogen species and will form a more durable finish on the textile material. Accordingly, the polymer preferably comprises an average of at least about 3 hindered amine moieties per polymer molecule, or at least about 3.5 hindered amine moieties per polymer molecule, or at least about 4 hindered amine moieties per polymer molecule, or at least about 4.5 hindered amine moieties per polymer molecule, or at least about 5 hindered amine moieties per polymer molecule.

The number of hindered amine moieties can also be expressed in terms of millimoles of hindered amine moieties per gram of polymer solid. Preferably, the polymer comprises at least about 1 millimoles of hindered amine moieties per gram of polymer solid, or at least about 1.5 millimoles of hindered amine moieties per gram of polymer solid, or at least about 2 millimoles of hindered amine moieties per gram of polymer solid, or at least about 2.5 millimoles of hindered amine moieties per gram of polymer solid, or at least about 3 millimoles of hindered amine moieties per gram of polymer solid.

Each of structures (VII)-(XI) shown below represents a hindered amine moiety useful as a starting material in the present processes. After the hindered amine compound is deposited onto a target textile substrate, as described herein, a reaction between the hindered amine and an oxidative halogen-containing solution occurs, in which the hydrogen atom attached directly to the nitrogen atom on the amine group is replaced with a halide atom (for example, a chlorine, bromine, or iodine atom).

Structure (VII)

In certain embodiments, the polymer comprises secondary, hindered amine moieties conforming to structure (VII):

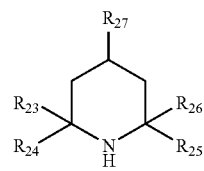

(VII)

In structure (VII), $R_{23}$, $R_{24}$, $R_{25}$, and $R_{26}$ are independently selected from the group consisting of $C_1$-$C_4$ alkyl groups, and $R_{27}$ is a group linking the hindered amine moiety attached to the polymer chain.

Suitable polymers comprising hindered amine moieties conforming to structure (VII) include, but are not limited to:

(i) a copolymer of N,N-bis-(2,2,6,6-tetramethyl-piperidin-4-yl)-propane-1,3-diamine, N,N-bis-(2,2,6,6-tetramethyl-piperidin-4-yl)-hexane-1,6-diamine, and N-butyl-2,2,6,6-tetramethylpiperidin-4-amine (CAS Registry Number 72076-41-6);

(ii) a copolymer of N-butyl-2,2,6,6-tetramethylpiperidin-4-amine, $N^1$-(2,2,6,6-tetramethylpiperidin-4-yl)-hexane-1,6-diamine, and 2,4,6-trichloro-[1,3,5]triazine (CAS Registry Number 72245-38-6);

(iii) a copolymer or homopolymer of 2,2,6,6-tetramethyl-piperidin-4-yl methacrylate;

(iv) a copolymer of 2,2,6,6,-tetramethyl-piperidin-4-amine, maleic anhydride, and $C_{20}$-$C_{24}$ alkenes (CAS Registry Number 152261-33-1);

(v) poly[(6-morpholino-s-triazine-2,4-diyl)[(2,2,6,6-tetramethyl-piperidin-4-yl)imino]-hexamethylene[(2,2,6,6-tetramethyl-piperidin-4-yl) imino)]] (CAS Registry Number 082451-48-7);

(vi) a copolymer of N,N-bis-(2,2,6,6-tetramethyl-piperidin-4-yl)-hexane-1,6-diamine, 2,4,6-trichloro-[1,3,5]triazine, and N-butyl-1-butanamine (CAS Registry Number 192268-64-7);
(vii) poly[(6-((1,1,3,3-tetramethylbutyl)amino)-1,3,5-triazine-2,4-diyl)((2,2,6,6-tetramethylpiperidin-4-yl)imino)-1,6-hexanediyl((2,2,6,6-tetramethyl-4-piperidinyl)imino)] (CAS Registry Number 71878-19-8);
(viii) a copolymer of N,N-bis-(2,2,6,6-tetramethyl-piperidin-4-yl)-hexane-1,6-diamine, 2,4,6-trichloro-[1,3,5]triazine, and 2,4,4-trimethyl-1,2-pentanamine (CAS Registry Number 70624-18-9);
(ix) a copolymer of N,N-bis-(2,2,6,6-tetramethyl-piperidin-4-yl)-hexane-1,6-diamine and morpholine-2,4,6-trichloro-[1,3,5]triazine (CAS Registry Number 193098-40-7); and
(x) combinations thereof.

Preferably, the polymer is selected from the group consisting of:
(i) poly[(6-morpholino-s-triazine-2,4-diyl)[(2,2,6,6-tetramethyl-piperidin-4-yl)imino]-hexamethylene [(2,2,6,6-tetramethyl-piperidin-4-yl)imino)]] (CAS Registry Number 082451-48-7);
(ii) a copolymer of 2,2,6,6,-tetramethyl-piperidin-4-amine, maleic anhydride, and $C_{20}$-$C_{24}$ alkenes (CAS Registry Number 152261-33-1);
(iii) poly[(6-((1,1,3,3-tetramethylbutyl)amino)-1,3,5-triazine-2,4-diyl)((2,2,6,6-tetramethyl-pipe ridin-4-yl)imino)-1,6-hexanediyl((2,2,6,6-tetramethyl-4-piperidinyl)imino)] (CAS Registry Number 71878-19-8);
(iv) a copolymer of N,N-bis-(2,2,6,6-tetramethyl-piperidin-4-yl)-hexane-1,6-diamine, 2,4,6-trichloro-[1,3,5]triazine, and N-butyl-1-butanamine (CAS Registry Number 192268-64-7); and
(v) combinations thereof.

Most preferably, the polymer is poly[(6-morpholino-s-triazine-2,4-diyl)[(2,2,6,6-tetramethyl-piperidin-4-yl)imino]-hexamethylene[(2,2,6,6-tetramethyl-piperidin-4-yl)imino)]] (CAS Registry Number 082451-48-7).

Structure (VIII)

The polymer utilized in the second embodiment of the treated textile can comprise secondary, hindered amine moieties conforming to structure (VIII):

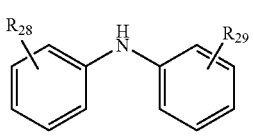

(VIII)

In structure (VIII), $R_{28}$ is selected from the group consisting of hydrogen atoms, alkyl groups, aryl groups, amine groups, amide groups, and combinations thereof. $R_{29}$ is a group linking the hindered amine moiety to the polymer chain.

Structure (IX)

The polymer utilized in the second embodiment of the treated textile material can comprise secondary hindered amine moieties conforming to structure (IX):

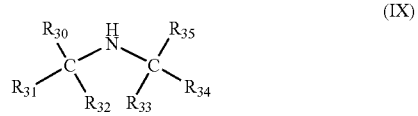

(IX)

In structure (IX), $R_{30}$, $R_{32}$, $R_{33}$, and $R_{35}$ are independently selected from the group consisting of $C_1$-$C_4$ alkyl groups. $R_3$, and $R_{34}$ are independently selected from the group consisting of an alkyl group, an aryl group, an amine group, an amide group, and combinations thereof, provided that at least one of $R_{31}$ and $R_{34}$ is a group linking the hindered amine moiety to the polymer chain.

Structure (X)

The polymer utilized in the second embodiment of the treated textile material can comprise secondary hindered amine moieties conforming to structure (X):

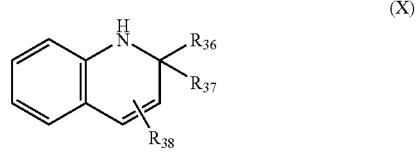

(X)

In structure (X), $R_{36}$ and $R_{37}$ are independently selected from the group consisting of $C_1$-$C_4$ alkyl groups, and $R_{38}$ is a group linking the hindered amine moiety to the polymer chain. Suitable polymers comprising hindered amine moieties conforming to structure (X) include, but are not limited to, a homopolymer or copolymer of 2,2,4-trimethyl-1,2-dihydroquinoline.

Structure (XI)

The polymer utilized in the second embodiment of the treated textile material can comprise secondary hindered amine moieties conforming to structure (XI):

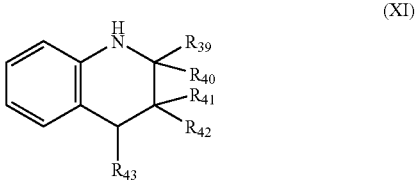

(XI)

In structure (XI), $R_{39}$, $R_{40}$, $R_{41}$, and $R_{42}$ are independently selected from the group consisting of $C_1$-$C_4$ alkyl groups, and $R_{43}$ is a group linking the hindered amine moiety to the polymer chain.

Methods to Produce Halamine Finish on Textile Substrate

Method (A)

In a first embodiment, the process comprises the steps of:
(a) dissolving a hindered amine compound in an aqueous solution by adding acid with to the hindered amine compound, thereby producing a solution containing up to about 30% by weight of solution of a protonated hindered amine compound;

(b) contacting a target textile substrate with the protonated hindered amine solution, for example, in the rinse cycle of a typical laundry process, thereby causing the protonated hindered amine to deposit on the surface of the textile substrate;

(c) deprotonating the hindered amine deposited on the target textile substrate by evaporating the acid used to protonate the hindered amine or by neutralizing the protonated hindered amine with an alkaline; and (d) reacting the deposited, deprotonated hindered amine with an oxidative halogen-containing solution (e.g., bleach), for example, in the rinse cycle, to form a hindered halamine on the textile substrate.

The target textile substrate may be laundered, or otherwise cleaned, before being subjected to the treatment process described above. Alternately, the treatment process described above may be successfully conducted using a conventional washing machine with a modified rinse cycle. The laundering may occur in an industrial setting or a home setting, using water temperatures that are appropriate for the type of textile fabric being laundered. The present process has been found effective at treating the entire wash loads of both industrial washing machines (typically, 16-pound loads) and home washing machines (typically, 4-pound loads). Any detergent may be used to launder the textile fabric, with preference being given to traditional detergents containing anionic surfactants and an alkaline pH. As used herein, the phrase "alkaline pH" or "basic pH" refers to a pH range of between about 8 and about 14. As will be understood, laundered substrates typically retain a residue of such surfactants at the beginning of the rinse cycle, such residue being used advantageously in the present process.

The antimicrobial finish applied to textile substrates treated according to the present methods has been observed to be surprisingly durable, even to industrial laundering processes. Industrial laundering processes typically are used by commercial laundry services to clean uniforms, hospital linens, towels, and linens used in hotels. Such industrial laundering processes differ from home laundering conditions in that they typically use more alkaline detergent solutions, higher washing temperatures, and harsher mechanical agitation. While not wishing to be bound to any particular theory, it is hypothesized that the durability of the treated textile material (i.e., the durability of the finish or coating on the treated textile material) is due, at least in part, to an affinity of the hindered halamine for the textile fiber and/or the lack of solubility of the hindered halamine during ordinary (high pH) laundry conditions.

Step (a) is the preparation of a solution containing a protonated hindered amine compound. The composition used to carry the hindered amine compound may be any suitable composition. For example, the hindered amine compound may be dissolved or suspended in an organic solvent. Alternatively, the hindered amine compound can be emulsified or dispersed in an aqueous carrier using an appropriate emulsifying or dispersing agent. Typically, such emulsions or dispersions are produced by subjecting a mixture of the hindered amine or compound, an emulsifying or dispersing agent, and an aqueous carrier to a high shear or milling process.

Preferably, however, the hindered amine compound is dissolved in an acidic aqueous solution (with or without an organic co-solvent) at a concentration of about 5 wt. % to about 60 wt. %, based on the total weight of the acidic aqueous solution. The acidic aqueous solution utilized in making the composition of the method may contain any suitable acid. Preferably, the acidic aqueous solution contains a volatile acid, such as citric acid, acetic acid, propionic acid, or hydrogen chloride. While not wishing to be bound to any particular theory, it is believed that the use of a volatile acid will allow the acid to be removed when the treated textile material is dried following application of the treatment composition. The acid may be added to the aqueous solution in any suitable amount. Typically, the amount of acid is an amount sufficient to protonate the hindered amine compound, thus making it soluble in the aqueous solution. The molar ratio of acid to hindered amine moieties typically is greater than about 1:1 to ensure the complete dissolution of the hindered amine, thereby forming a stable solution.

Step (b) involves contacting the target textile substrate with the protonated hindered amine compound, for example, during the rinse cycle of the laundering process. The presence of rinse water during the cycle tends to increase the pH of the solution, while reducing the concentration of the protonated hindered amine solution. As a result of the pH change (and, to a lesser extent, the presence of anionic surfactants), the protonated hindered amine compound precipitates out of the rinse water solution and deposits onto the surface of the textile substrate, thereby becoming at least partially deprotonated. The amount of deprotonated hindered amine deposited on the textile substrate may range from about 0.1% to about 5% by weight, based on the weight of the untreated substrate.

Step (c) is the deprotonation of the deposited hindered amine compound, either by using an alkaline solution (for example, as is present as the result of residual detergent found in a laundry rinse cycle) or by evaporating the acid (for example, in a tumble dryer).

Step (d) is the addition of an oxidative halogen-containing solution, as defined previously, to the textile substrate containing the deprotonated hindered amine. One such example is a hypohalite solution, for example, hypochlorite bleach. When conducted in a laundry rinse cycle, the addition of the oxidative halogen-containing solution further increases the pH of the rinse water, causing more precipitation of the hindered amine compound onto the textile substrate. As the hindered amine compounds are deposited and deprotonated, the halogen component of the oxidative halogen-containing solution reacts with the hindered amine compound, replacing the hydrogen atom attached directly to the amine group and creating a hindered halamine compound. Such hindered halamine compound is water insoluble at high pH, making it durable to repeated launderings.

In practice, Method (A) may be conducted, for example, as follows. In one embodiment, a typical load of textile garments and/or sheets are laundered in a conventional household washing machine, using a powdered laundry detergent resulting in a pH of the laundry solution of about 11. A polymeric hindered amine compound having about 5 hindered amine moieties per molecule and an average molecular weight of about 3,000 atomic units is protonated and dissolved in an aqueous acetic acid solution at a pH of about 3. The textile articles are agitated with the detergent, after which the basin is drained. As soon as the basin is refilled with clean rinse water, the protonated hindered amine solution is added. The pH difference between the rinse water (which is alkaline due to the presence of residual detergent) and the acidic amine solution causes deposition of the hindered amine compound onto the textile articles. A cup of chlorine bleach is subsequently added to the rinse water/hindered amine solution to further increase the pH to above 7 and to allow the reaction of the oxidative chlorine in the bleach with the hindered amine deposited on the surface of the textile articles. The rinse water is then drained from the basin and the textile articles are spun to remove excess water. The treated textile articles are finally removed from the washing machine and dried in a conventional household tumble dryer at a setting appropriate for the fiber type of the textile articles. The textile articles treated using this method (that is, Method (A)) typically retain between 1 ppm and 2,000 ppm of active chlorine on the surface thereof, depending on the ratio of hindered amine to chlorine bleach, the loading level of the washing machine, and the amount of hindered amine deposited on the surface of the textile articles. Active chlorine levels of between about 10 ppm and about 2,000 ppm are believed to be sufficient to provide antimicrobial properties to the treated textile articles.

Method (B)

In an alternate embodiment, where hydrogen peroxide is used in place of chlorine bleach, steps (a) through (c) are the same as those provided above, with regard to Method (A). In step (d), a halide salt (such as sodium chloride) is added with hydrogen peroxide in place of the oxidative halogen-containing solution, thus producing an oxidative halogen-containing solution in situ. Accordingly, step (d) is as follows: adding a halide salt and hydrogen peroxide to the rinse cycle to promote precipitation of the protonated hindered amine onto the textile surface and to react with the deprotonated hindered amine to form a hindered halamine on the textile surface. In this embodiment, the halogen converted from the salt reacts with the deprotonated hindered amine to form a hindered halamine.

Method (C)

In yet another embodiment, such as may occur in a manufacturing environment, the process comprises the steps of:

(a) preparing an aqueous bath containing from about 0.02% by weight to about 5.0% by weight of solution of a protonated hindered amine compound, where the aqueous bath further contains an acid that lowers the pH of the bath and assists in solubilizing the protonated hindered amine compound;

(b) impregnating a target textile substrate with the solution in the bath of (b);

(c) drying the textile substrate to volatilize the acid and deprotonate the amine compound, thereby causing precipitation of the deprotonated amine compound onto the surface of the textile substrate;

(d) applying an oxidative halogen-containing solution, or a combination of hydrogen peroxide and a halide salt, to the textile substrate to react with the deprotonated hindered amine and form a hindered halamine.

Steps (a) through (d) are preferably performed sequentially.

The bath of step (a) contains sufficient amounts of hindered amine compound to treat the target substrates. The temperature of the bath is preferably between room temperature (about 70° F.) and about 160° F. The bath may further contain wicking agents, anti-soil deposition agents, and the like, if so desired.

Step (b) involves subjecting the target substrate to immersion in the bath containing the protonated hindered amine compound. Transporting the substrate into and through the bath may be accomplished by any conventional means, such as rollers, conveyors, or the like. The time that the substrate is immerged in the bath is not critical, so long as the substrate is fully impregnated with the hindered amine compound. Excess hindered amine solution may be removed by squeezing, spinning, or other similar techniques known to those of skill in the art. The wet add-on level of the hindered amine compound on the textile substrate may range from about 30% to about 150%, based on the dry weight of the textile substrate.

Step (c) involves drying the treated substrate to volatilize the acid and to deprotonate the hindered amine compound, thus causing the hindered amine compound to be precipitated onto the surface of the substrate. Such drying may be accomplished by any conventional means, such as convection ovens, microwave ovens, infrared ovens, steam cans, and the like. Drying is preferably done using a convection oven at temperatures between 120° F. and 420° F. for periods ranging from 1 minute to 200 minutes. Typically, about 0.1% and about 5% by weight of hindered amine, based on the weight of the untreated textile substrate, may be deposited in this manner without negatively affecting the hand of the substrate.

Step (d) involves the application of an oxidative halogen-containing solution (or, alternately, a solution containing both hydrogen peroxide and a halide salt) to the dried substrate. The solution may be applied by spraying, dipping, wiping, coating, and the like. As a result, a halogen of the oxidative halogen-containing solution or the halide salt solution reacts with the deprotonated hindered amine to form the desired halamine compound.

While the above-described processes have discussed the production of chlorine-containing amines, the treated textile material may be rendered antimicrobial by exposing the treated textile material to an iodine-containing solution. While not wishing to be bound to any particular theory, it is believed that the iodine reacts with the secondary hindered amine moieties present on the polymer in the finish to produce an "iodo-amine" or an iodine-amine complex. This iodoamine or an iodine-amine complex has been observed to exhibit a light yellow color, which can act as a visual indication of the formation of the antimicrobial iodo-amine or iodine-amine complex on a textile material that has been so treated. Furthermore, the iodo-amine or iodine-amine complex has been observed to exhibit relatively good wash durability.

In order to lessen the potential irritation to persons utilizing the treated textile materials described herein, the textile material preferably is rinsed after it is exposed to the oxidative halogen solution. The treated textile material can be rinsed in water alone; however, the treated textile material preferably is rinsed with a solution containing a reducing agent, such as those described in U.S. Pat. Nos. 6,482,756 (Li) and 6,576,154 (Li), which are hereby incorporated by reference. While not wishing to be bound to any particular theory, it is believed that rinsing with a suitable reducing agent will significantly reduce the amount of the oxidative halogen retained by the fabric itself (e.g., the oxidative halogen retained by the fibers themselves) without significantly reducing the amount of halamines formed by the reaction of the hindered amine moieties contained in the finish with the oxidative halogen solution. Indeed, the halamines formed in the finish of the treated textile have been found to be relatively stable to rinsing with a reducing agent.

The following examples further illustrate the present process but, of course, should not be construed as in any way limiting the scope of the subsequent claims.

Example 1

A hindered amine solution was prepared by combining the following components, with stirring:

| | |
|---|---|
| CHIMASSORB ® 2020 hindered amine compound (available from Ciba Specialty Chemicals): | 1 gram |
| Acetic acid: | 0.5 grams |
| Water: | 93.5 grams |

To this clear solution were added the following components:

| | |
|---|---|
| LUBRIL® QCX hydrophilic polyester soil release resin (available from Rhodia): | 4 grams |
| DOUSOFT® 1062 softening agent (available from Boehme Filatex): | 0.8 grams |

CHIMOSSORB® 2020 is described by the manufacturer as a secondary, hindered amine compound described as the reaction product of 1,6-hexanediamine, N,N'-bis(2,2,6,6-tetramethyl-4-piperidinyl)-polymer; 2,3,6-trichloro-1,3,5-triazine; N-butyl-1-butanamine; and N-butyl-2,2,6,6-tetramethyl-4-piperidinamine (CAS Number 192268-64-7).

Knitted gloves having a fiber content of 60% cotton and 40% polyester was saturated with the above solution. The gloves were passed through a pair of nip rolls at a pressure of about 35 p.s.i. to remove excess treatment solution. The gloves exhibited a wet pick-up of about 64% by weight as compared to the dry weight of the gloves.

The saturated gloves were then dried in a conventional household tumble dryer, set on a cotton setting, for 60 minutes.

After drying, the gloves were washed in an industrial laundry process using an alkaline detergent solution, in which about one cup of regular chlorine bleach (6% hypochlorite solution sold under the tradename CLOROX® by The Clorox Company) was added during the rinse cycle. Also included with the treated gloves were several gloves that untreated, which were used as a Control.

The treated gloves were then dried and evaluated for active chlorine levels using the technique described below.

A sample of the gloves were evaluated for active chlorine content after 1 wash, a sample of the gloves were evaluated for active chlorine content after 10 washes, and the remainder were evaluated after 25 washes.

Example 2

Example 2 was prepared identically to Example 1, except that 2 grams of CHIMASSORB® 2020 were used to form the hindered amine solution.

Example 3

A hindered amine solution was prepared by combining the following components, with stirring:

| | |
|---|---|
| CHIMASSORB® 2020 hindered amine compound (available from Ciba Specialty Chemicals): | 0.4% by weight |
| Acetic acid: | 0.2% by weight |
| LUBRIL® QCX hydrophilic polyester soil release resin (available from Rhodia): | 1.6% by weight |
| DOUSOFT® 1062 softening agent (available from Boehme Filatex): | 0.32% by weight |
| Water: | 97.48% by weight |

The hindered amine solution was charged into the rinse cycle of a household washing machine. The water supply to the washing machine was turned off to prevent additional water from being charged into the solution (thus diluting the solution). Several pairs of gloves were added to the solution. After mechanical agitation, drainage of the hindered amine solution, and spinning, the washing machine was stopped.

The gloves were weighed to determine their wet pick-up. The gloves weighed 150% of the dry weight of the untreated gloves.

The gloves were then dried in a conventional household tumble dryer, set at a cotton setting, for 60 minutes.

After drying, the gloves were washed in an industrial washing machine using an alkaline detergent solution, in which about one cup of chlorine bleach (6% hypochlorite solution sold under the tradename CLOROX® by The Clorox Company) was added during the rinse cycle. A sample of the gloves were evaluated for active chlorine content after 1 wash and the remainder of the gloves were evaluated for active chlorine content after 10 washes. During the subsequent washes, bleach was not added during the rinse cycle.

The fabric of the gloves of Examples 1-3 were evaluated for active chlorine content, an indicator of antimicrobial properties.

Measurement of Active Chlorine Present on Example Fabrics

The samples were then tested to determine active chlorine content of the laundered samples. The active chlorine content was determine by first cutting a small piece of fabric from each of Examples 1-3 and weighing each fabric piece to determine its mass in grams ($W_{fabric}$). Each of the fabric pieces was then cut into small strips measuring approximately 5 mm by 2 mm so that the fabric pieces could be easily placed into a solution for titration. The strips for each fabric piece were then placed in separate flasks, and 25 ml of a 0.05 N solution of sulfuric acid and 50 ml of deionized water were added to each flask. Next, approximately 1.5 g of potassium iodide was added to each flask, and the flasks were sealed and stirred at room temperature for approximately 30 minutes. The solution contained in each flask was then titrated with a standard sodium thiosulfate solution having a concentration ($C_{standard}$) of approximately 0.001 M until the solution turned a light yellow color. Approximately 1 ml of a 1% starch solution was then added to each flask, at which point the solution turned a blue color. The solution contained in each flask was then titrated further with the standard sodium thiosulfate solution until it was colorless. The final volume of the standard sodium thiosulfate solution added ($V_{standard}$) was then recorded. Using the values obtained from the above-described titration, the active chlorine content ($C_{Cl}$) of each sample in parts-per-million (grams of active chlorine per million grams of the fabric sample) was then determined using the following equation:

$$C_{Cl} = \frac{1.775 \times 10^7 \times C_{standard} \times V_{standard}}{W_{fabric}}$$

The active chlorine content for each of Examples 1-3 determined using the above-described titration method and calculation are set forth in TABLE 1 below.

TABLE 1

Measured active chlorine content (ppm) for Examples 1-3

| Sample Identification | After 1 wash | After 10 washes | After 25 washes |
|---|---|---|---|
| Control (Example 1) | 27 | 22 | 0 |
| Example 1 | 185 | 158 | 132 |
| Example 2 | 288 | 256 | 233 |
| Example 3 | 310 | 201 | not measured |

The treated fabrics of Examples 1-3 exhibited a significant amount of active chlorine, and the treatments exhibited durability to multiple launderings.

It has also been discovered that the amount of active chlorine on a target substrate may be increased by repeating the process steps of providing an acidic hindered amine solution, depositing the hindered amine compound from the solution onto the target substrate, evaporating or neutralizing the acid used to protonate the hindered amine, and reacting the deposited hindered amine compound with an oxidative halogen-containing solution. Such findings are exhibited by Examples 4-7 below.

Examples 4-6

A hindered amine solution was prepared by combining the following components, with stirring:

| | |
|---|---|
| LOWILITE ® 94 polymeric hindered amine compound (available from Great Lakes Polymer Additives): | 3.0% by weight |
| Acetic acid: | 3.0% by weight |

LOWILITE® 94 is described by the manufacturer as a Hindered Amine Light Stabilizer (HALS) that protects organic polymers against the degradation caused by exposure to ultraviolet radiation. The hindered amine is the reaction product of N,N'-Bis(2,2,6,6-tetramethyl-4-piperidinyl)-1,6-hexanediamine polymer with 2,4,6-trichloro-1,3,5-triazene and 2,4,4-timethyl-1,2-pentanamine (CAS Reg. Number 70624-18-9).

Four different fabrics (Examples 4-6) were used as target textile substrates. The fabrics are described as follows:

Example 4: 65% polyester/35% cotton blend; plain woven; 4.5 ounces/yard$^2$

Example 5: 65% polyester/35% cotton blend; 2×1 left-hand twill woven; 8 ounces/yard$^2$ Example 6: 100% polyester; 2×1 left-hand twill woven; 7 ounces/yard$^2$ For each trial, four pounds of the Example fabric were laundered in a 16-gallon household washing machine using a powdered laundry detergent (alkaline pH). The laundering process was allowed to proceed as normal until the rinse cycle. When the basin filled with rinse water, 100 grams of the hindered amine solution was charged into the rinse solution.

After approximately 2 minutes of agitation, 6 ounces of chlorine bleach (6% hypochlorite solution sold under the tradename CLOROX® by The Clorox Company) were added.

The rinse water was then drained and the treated fabrics were spun to remove excess water. The target fabrics were then dried for about 15 minutes and evaluated for active chlorine levels, using the test method described above for Examples 1-3.

For each fabric, the process was repeated, including addition of hindered amine solution and bleach, to determine active chlorine levels after three cycles and five cycles. The results are shown in TABLE 2 below.

TABLE 2

Measured active chlorine content (ppm) for Examples 4-6 with addition of hindered amine and chlorine after each cycle

| Sample Identification | After 1 cycle | After 3 cycles | After 5 cycles |
|---|---|---|---|
| Example 4 | 66.6 | 124.4 | 197 |
| Example 5 | 64.6 | 103.4 | 149 |
| Example 6 | 54.2 | 82.9 | 112 |

The treated fabrics of Examples 4-6 exhibited a significant amount of active chlorine, and the repeated treatments increased the amount of active chlorine present on the target substrates.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the present process to be practiced otherwise than as specifically described herein. Accordingly, this disclosure is intended to include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for treating a textile substrate, the method comprising the steps of:
    (a) dissolving a hindered amine compound in an aqueous solution by adding acid to the hindered amine compound, thereby producing a solution containing up to about 30% by weight of solution of a protonated hindered amine compound;
    (b) contacting a target textile substrate with the protonated hindered amine solution, thereby causing the protonated hindered amine to deposit on the surface of the textile substrate;
    (c) deprotonating the hindered amine deposited on the target textile substrate by neutralizing the protonated hindered amine with an alkaline; and (d) reacting the deposited, deprotonated hindered amine with an oxidative halogen-containing solution to form a hindered halamine on the textile substrate.

2. The method of claim 1, wherein the yarns or fibers comprise a fiber selected from the group consisting of cellulose, cellulose acetate, polyamides, polyesters, polyethylenes, polypropylenes, polyacrylics, and combinations thereof.

3. The method of claim 1, wherein the hindered amine compound of step (a) has a structure conforming the following:

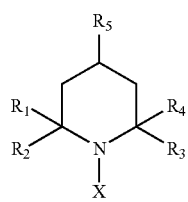

(I)

wherein $R_1$, $R_2$, $R_3$, and $R_4$ are independently selected from the group consisting of $C_1$-$C_4$ alkyl groups; $R_5$ is selected from the group consisting of a hydrogen atom, an alkyl group, an alkyl amine group, a cyclic amine group, an amide group, a cyclic amide group, an isocyanate group, a hydroxyl group, an ether group, an ester group, and combinations thereof; and wherein X is a hydrogen atom.

4. The method of claim 1, wherein the hindered amine compound of step (a) has a structure conforming the following:

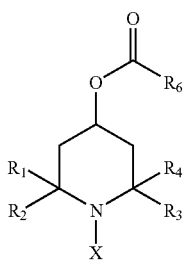

(II)

wherein $R_1$, $R_2$, $R_3$, and $R_4$ are independently selected from the group consisting of $C_1$-$C_4$ alkyl groups; $R_6$ is a $C_{11}$-$C_{20}$ alkyl group; and X is a hydrogen atom.

5. The method of claim 1, wherein the hindered amine compound of step (a) has a structure conforming the following:

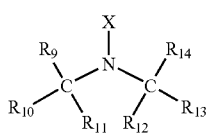

(IV)

wherein $R_9$, $R_{11}$, $R_{12}$, and $R_{14}$ are independently selected from the group consisting of $C_1$-$C_4$ alkyl groups; $R_{10}$ and $R_{13}$ are independently selected from the group consisting of an alkyl group, an aryl group, an amine group, an amide group, and combinations thereof; and X is a hydrogen atom.

6. The method of claim 1, wherein the hindered amine compound comprises a plurality of hindered amine moieties, said hindered amine moieties conforming to the structure (VII):

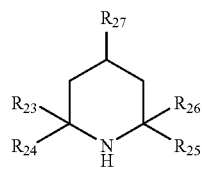

(VII)

wherein $R_{23}$, $R_{24}$, $R_{25}$, and $R_{26}$ are independently selected from the group consisting of $C_1$-$C_4$ alkyl groups and $R_{27}$ is a group linking the hindered amine moiety to the remainder of the hindered amine compound.

7. The method of claim 1, the hindered amine compound comprises a plurality of hindered amine moieties, said hindered amine moieties conforming to the structure (VIII):

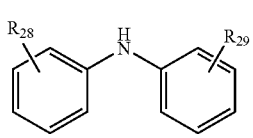

(VIII)

wherein $R_{28}$ is selected from the group consisting of hydrogen atoms, alkyl groups, aryl groups, amine groups, amide groups, and combinations thereof, and $R_{29}$ is a group linking the hindered amine moiety to the remainder of the hindered amine compound.

8. The method of claim 1, the hindered amine compound comprises a plurality of hindered amine moieties, said hindered amine moieties conforming to the structure (IX):

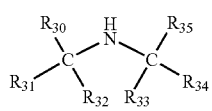

(IX)

wherein $R_{30}$, $R_{32}$, $R_{33}$, and $R_{35}$ are independently selected from the group consisting of $C_1$-$C_4$ alkyl groups, $R_{31}$ and $R_{34}$ are independently selected from the group consisting of an alkyl group, an aryl group, an amine group, amide groups, and combinations thereof, and wherein at least one of $R_{31}$ and $R_{34}$ is a group linking the hindered amine moiety to the remainder of the hindered amine compound.

9. The method of claim 1, the hindered amine compound comprises a plurality of hindered amine moieties, said hindered amine moieties conforming to the structure (X):

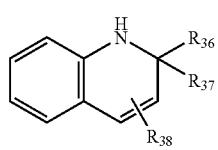

(X)

wherein $R_{36}$ and $R_{37}$ are independently selected from the group consisting of $C_1$-$C_4$ alkyl groups and $R_{38}$ is a group linking the hindered amine moiety to the remainder of the hindered amine compound.

10. The method of claim 1, the hindered amine compound comprises a plurality of hindered amine moieties, said hindered amine moieties conforming to the structure (XI):

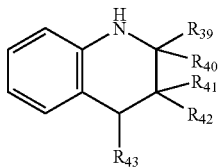

(XI)

wherein $R_{39}$, $R_{40}$, $R_{41}$, and $R_{42}$ are independently selected from the group consisting of $C_1$-$C_4$ alkyl groups, and $R_{43}$ is a group linking the hindered amine moiety to the remainder of the hindered amine compound.

11. The method of claim 6, wherein the hindered amine compound comprises an average of at least 3 hindered amine moieties per molecule.

12. The method of claim 7, wherein the hindered amine compound comprises an average of at least 4 hindered amine moieties per molecule.

13. The method of claim 1, wherein step (b) occurs during the rinse cycle of a laundry process.

14. The method of claim 1, wherein step (b) occurs in a bath.

15. The method of claim 1, wherein the oxidative halogen-containing solution of step (d) is selected from the group consisting of solutions of sodium hypochlorite, potassium hypobromite, sodium perchlorate, chlorine oxide, sodium periodate, iodine, bromine, and combinations thereof.

16. The method of claim 8, wherein the oxidative halogen-containing solution is a solution of sodium hypochlorite.

17. The method of claim 1, wherein the oxidative halogen-containing solution of step (d) is formed in situ as a solution of a halide salt and hydrogen peroxide.

* * * * *